United States Patent
Hammill, Sr. et al.

(10) Patent No.: US 8,465,530 B2
(45) Date of Patent: *Jun. 18, 2013

(54) LOCKING POLYAXIAL BALL AND SOCKET FASTENER

(75) Inventors: John E. Hammill, Sr., Maumee, OH (US); Robert L. Doubler, Monroe, MI (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/102,453

(22) Filed: May 6, 2011

(65) Prior Publication Data

US 2011/0208251 A1 Aug. 25, 2011

Related U.S. Application Data

(63) Continuation of application No. 12/355,145, filed on Jan. 16, 2009, now Pat. No. 7,947,065.

(60) Provisional application No. 61/114,515, filed on Nov. 14, 2008.

(51) Int. Cl.
*A61B 17/86* (2006.01)

(52) U.S. Cl.
USPC .......................................... 606/308; 606/266

(58) Field of Classification Search
USPC ........................ 606/246, 264–275, 305–308
See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | McConnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |
| 4,854,304 A | 8/1989 | Zielke |
| 4,867,144 A | 9/1989 | Karas et al. |
| 4,887,595 A | 12/1989 | Heinig et al. |

(Continued)

FOREIGN PATENT DOCUMENTS

| | | |
|---|---|---|
| DE | 69311928 | 2/1992 |
| DE | G9202745.8 | 6/1992 |

(Continued)

*Primary Examiner* — Kevin T Truong
*Assistant Examiner* — Michael Araj
(74) *Attorney, Agent, or Firm* — McHale & Slavin, P.A.

(57) ABSTRACT

A polyaxial ball and socket joint that can be locked into a fixed position. The fastening system consists of the polyaxial ball and socket joint used in conjunction with a bone screw having threads on one end for use in anchoring to the spine and a spherical connector on the other end operating as a pivot point about which a connecting assembly moves in a polyaxial fashion. A substantially U-shaped connecting assembly has a lower receptacle that operates as a socket for housing an upper retainer ring and a lower split retaining ring. The socket is receptive to the spherical connector which is inserted through the lower split retainer ring causing a momentary displacement thereof which allows for the positioning of the spherical connector between the upper and lower retainer rings.

25 Claims, 17 Drawing Sheets

U.S. PATENT DOCUMENTS

| | | |
|---|---|---|
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,177 A | 7/1992 | Miller |
| 5,133,716 A | 7/1992 | Plaza |
| 5,133,717 A | 7/1992 | Chopin |
| 5,176,678 A | 1/1993 | Tsou |
| 5,207,678 A | 5/1993 | Harms et al. |
| 5,217,497 A | 6/1993 | Mehdian |
| 5,257,993 A | 11/1993 | Asher et al. |
| 5,261,909 A | 11/1993 | Sutterlin et al. |
| 5,261,912 A | 11/1993 | Frigg |
| 5,312,404 A | 5/1994 | Asher et al. |
| 5,312,405 A | 5/1994 | Korotko et al. |
| 5,330,477 A | 7/1994 | Crook |
| 5,360,431 A | 11/1994 | Puno et al. |
| 5,364,399 A | 11/1994 | Lowery et al. |
| 5,395,371 A | 3/1995 | Miller et al. |
| 5,429,639 A | 7/1995 | Judet |
| 5,437,671 A | 8/1995 | Lozier et al. |
| 5,443,467 A | 8/1995 | Biedermann et al. |
| 5,466,237 A | 11/1995 | Byrd, III et al. |
| 5,470,333 A | 11/1995 | Ray |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,496,321 A | 3/1996 | Puno et al. |
| 5,498,262 A | 3/1996 | Bryan |
| 5,498,263 A | 3/1996 | DiNello et al. |
| 5,501,684 A | 3/1996 | Schlapfer et al. |
| 5,520,690 A | 5/1996 | Errico et al. |
| 5,527,314 A | 6/1996 | Brumfield et al. |
| 5,531,746 A | 7/1996 | Errico et al. |
| 5,545,164 A | 8/1996 | Howland |
| 5,549,608 A | 8/1996 | Errico et al. |
| 5,554,157 A | 9/1996 | Errico et al. |
| 5,562,661 A | 10/1996 | Yoshimi et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,601,553 A | 2/1997 | Trebing et al. |
| 5,607,426 A | 3/1997 | Ralph et al. |
| 5,609,593 A | 3/1997 | Errico et al. |
| 5,609,594 A | 3/1997 | Errico et al. |
| 5,628,740 A | 5/1997 | Mullane |
| 5,643,261 A | 7/1997 | Schafer et al. |
| 5,643,265 A | 7/1997 | Errico et al. |
| 5,647,873 A | 7/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,681,319 A | 10/1997 | Biedermann et al. |
| 5,688,272 A | 11/1997 | Montague et al. |
| 5,688,273 A | 11/1997 | Errico et al. |
| 5,690,630 A | 11/1997 | Errico et al. |
| 5,716,355 A | 2/1998 | Jackson et al. |
| 5,716,356 A | 2/1998 | Biedermann et al. |
| 5,716,357 A | 2/1998 | Rogozinski |
| 5,725,528 A | 3/1998 | Errico et al. |
| 5,725,588 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,810,818 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,947,966 A | 9/1999 | Drewry et al. |
| 5,954,725 A | 9/1999 | Sherman et al. |
| 5,961,517 A | 10/1999 | Biedermann et al. |
| 5,964,760 A | 10/1999 | Richelsoph |
| 5,980,523 A | 11/1999 | Jackson |
| 6,010,503 A | 1/2000 | Richelsoph et al. |
| 6,015,409 A | 1/2000 | Jackson |
| 6,019,759 A | 2/2000 | Rogozinski |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,080,156 A | 6/2000 | Asher et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,600 A | 9/2000 | Drummond et al. |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,261,287 B1 | 7/2001 | Metz-Stavenhagen |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,383,190 B1 | 5/2002 | Preissman |
| 6,402,752 B2 | 6/2002 | Schaffler-Wachter et al. |
| 6,436,100 B1 | 8/2002 | Berger |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,537,276 B2 | 3/2003 | Metz-Stavenhagen |
| 6,547,789 B1 | 4/2003 | Ventre et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |

| Patent No. | Date | Name |
|---|---|---|
| 6,565,565 B1 | 5/2003 | Yuan et al. |
| 6,565,567 B1 | 5/2003 | Haider |
| 6,582,436 B2 | 6/2003 | Schlapfer |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,641,586 B2 | 11/2003 | Varieur |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2* | 12/2003 | Barker et al. ............... 606/328 |
| 6,663,632 B1 | 12/2003 | Frigg |
| 6,663,635 B2 | 12/2003 | Frigg et al. |
| 6,672,788 B2 | 1/2004 | Hathaway |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,830 B2 | 6/2004 | Minfelde et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,905,500 B2 | 6/2005 | Jeon et al. |
| 6,932,817 B2 | 8/2005 | Baynham et al. |
| 6,945,972 B2 | 9/2005 | Frigg et al. |
| 6,950,997 B2 | 9/2005 | Dickey et al. |
| 6,951,561 B2 | 10/2005 | Warren et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| RE39,089 E | 5/2006 | Ralph et al. |
| 7,066,937 B2 | 6/2006 | Shluzas |
| 7,087,057 B2 | 8/2006 | Konieczynski et al. |
| 7,128,743 B2 | 10/2006 | Metz-Stavenhagen |
| 7,144,396 B2 | 12/2006 | Shluzas |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,445,627 B2* | 11/2008 | Hawkes et al. ............... 606/269 |
| 7,604,656 B2 | 10/2009 | Shluzas |
| 7,682,377 B2 | 3/2010 | Konieczynski et al. |
| 7,857,834 B2* | 12/2010 | Boschert ............... 606/269 |
| 7,875,065 B2* | 1/2011 | Jackson ............... 606/305 |
| 7,879,075 B2 | 2/2011 | Shluzas |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,173 B2 | 5/2011 | Hammill, Sr. et al. |
| 8,075,603 B2 | 12/2011 | Hammill, Sr. et al. |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0082602 A1 | 6/2002 | Biedermann et al. |
| 2002/0103487 A1 | 8/2002 | Errico et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0004512 A1 | 1/2003 | Farris et al. |
| 2003/0023243 A1 | 1/2003 | Biedermann et al. |
| 2003/0045879 A1 | 3/2003 | Minfelde et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0118395 A1 | 6/2003 | Abels et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0024464 A1 | 2/2004 | Errico et al. |
| 2004/0092934 A1 | 5/2004 | Howland |
| 2004/0097933 A1* | 5/2004 | Lourdel et al. ............... 606/61 |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0181224 A1 | 9/2004 | Biedermann et al. |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033289 A1 | 2/2005 | Warren et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131409 A1 | 6/2005 | Chervitz et al. |
| 2005/0131413 A1 | 6/2005 | O'Driscoll et al. |
| 2005/0131537 A1 | 6/2005 | Hoy et al. |

| | | |
|---|---|---|
| 2005/0131538 A1 | 6/2005 | Chervitz et al. |
| 2005/0131545 A1 | 6/2005 | Chervitz et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192579 A1 | 9/2005 | Jackson |
| 2005/0192580 A1 | 9/2005 | Dalton |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228392 A1 | 10/2005 | Keyer et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagen et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0015105 A1 | 1/2006 | Warren et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0084979 A1 | 4/2006 | Jackson |
| 2006/0084981 A1 | 4/2006 | Shluzas |
| 2006/0149240 A1 | 7/2006 | Jackson |
| 2006/0149241 A1 | 7/2006 | Richelsoph et al. |
| 2006/0155277 A1 | 7/2006 | Metz-Stavenhagen |
| 2006/0173456 A1 | 8/2006 | Hawkes et al. |
| 2006/0235392 A1 | 10/2006 | Hammer et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0276791 A1 | 12/2006 | Shluzas |
| 2006/0293665 A1 | 12/2006 | Shluzas |
| 2007/0049933 A1 | 3/2007 | Ahn et al. |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi |
| 2008/0009862 A1 | 1/2008 | Hoffman |
| 2008/0015576 A1 | 1/2008 | Whipple |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0086132 A1 | 4/2008 | Biedermann et al. |
| 2008/0097436 A1 | 4/2008 | Culbert et al. |
| 2008/0177322 A1 | 7/2008 | Davis et al. |
| 2008/0269809 A1 * | 10/2008 | Garamszegi ................. 606/305 |
| 2008/0287998 A1 | 11/2008 | Doubler et al. |
| 2009/0163956 A1 | 6/2009 | Biedermann et al. |
| 2010/0023061 A1 | 1/2010 | Randol et al. |
| 2010/0312288 A1 | 12/2010 | Hammill, Sr. et al. |

FOREIGN PATENT DOCUMENTS

| | | |
|---|---|---|
| DE | 19509332 | 8/1996 |
| DE | 19507141 | 9/1996 |
| DE | 19720782 | 11/1998 |
| EP | 0147050 | 2/1988 |
| EP | 1121902 | 8/2001 |
| EP | 1190678 | 3/2002 |
| EP | 1474050 | 11/2004 |
| EP | 1570816 | 3/2005 |
| EP | 1570795 | 9/2005 |
| EP | 1579816 | 9/2005 |
| EP | 1634537 | 3/2006 |
| FR | 2729291 | 7/1996 |
| FR | 27966545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 1/2005 |
| FR | 2865378 | 7/2005 |
| GB | 2173104 | 10/1986 |
| GB | 2365345 | 2/2002 |
| WO | WO0149191 | 7/2001 |
| WO | WO02054966 | 7/2002 |
| WO | WO03068083 | 8/2003 |
| WO | WO03068088 | 8/2003 |
| WO | WO2004041100 | 5/2004 |
| WO | WO2004089245 | 10/2004 |
| WO | WO2004107997 | 12/2004 |
| WO | WO2005000136 | 1/2005 |
| WO | WO2005000137 | 1/2005 |
| WO | WO2005020829 | 3/2005 |
| WO | WO2005072632 | 8/2005 |
| WO | WO2005082262 | 9/2005 |
| WO | WO2005099400 | 10/2005 |
| WO | WO2006012088 | 2/2006 |
| WO | WO2006017616 | 2/2006 |
| WO | WO2006028537 | 3/2006 |
| WO | WO2010056846 A2 | 5/2010 |
| WO | WO2010056846 A3 | 5/2010 |
| WO | WO2011097431 | 8/2011 |
| WO | WO2012006554 A2 | 1/2012 |

* cited by examiner

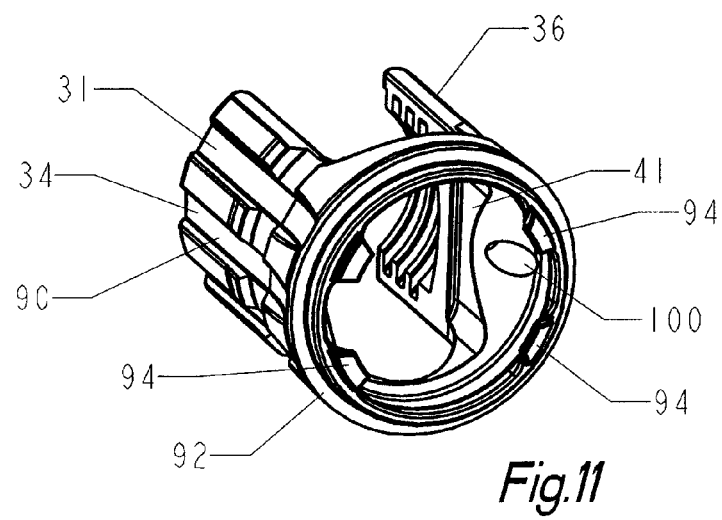
Fig.11
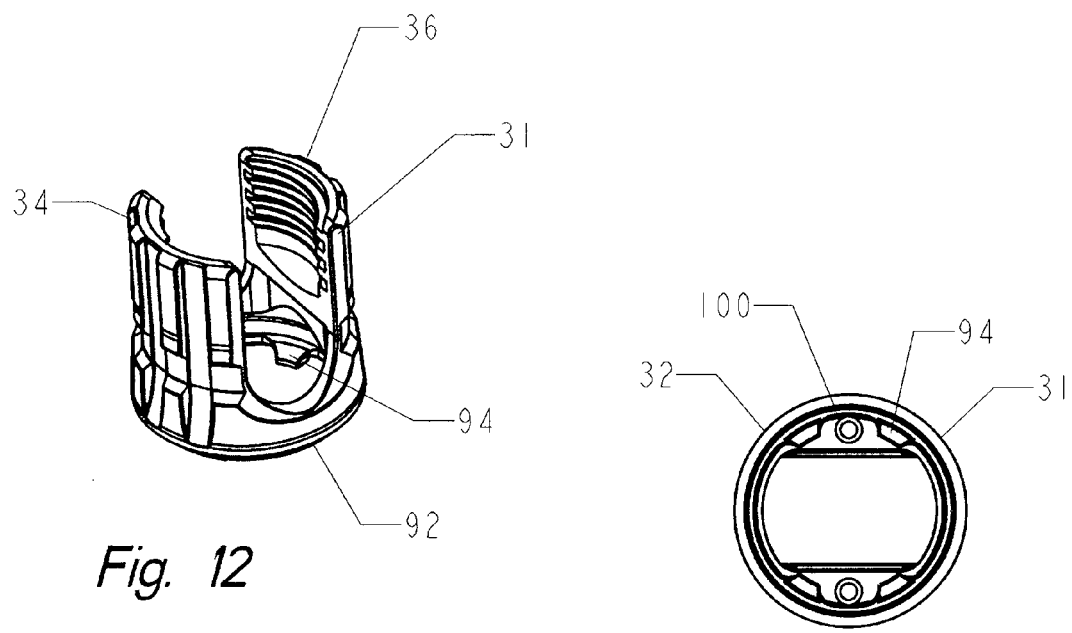
Fig. 12
Fig. 13

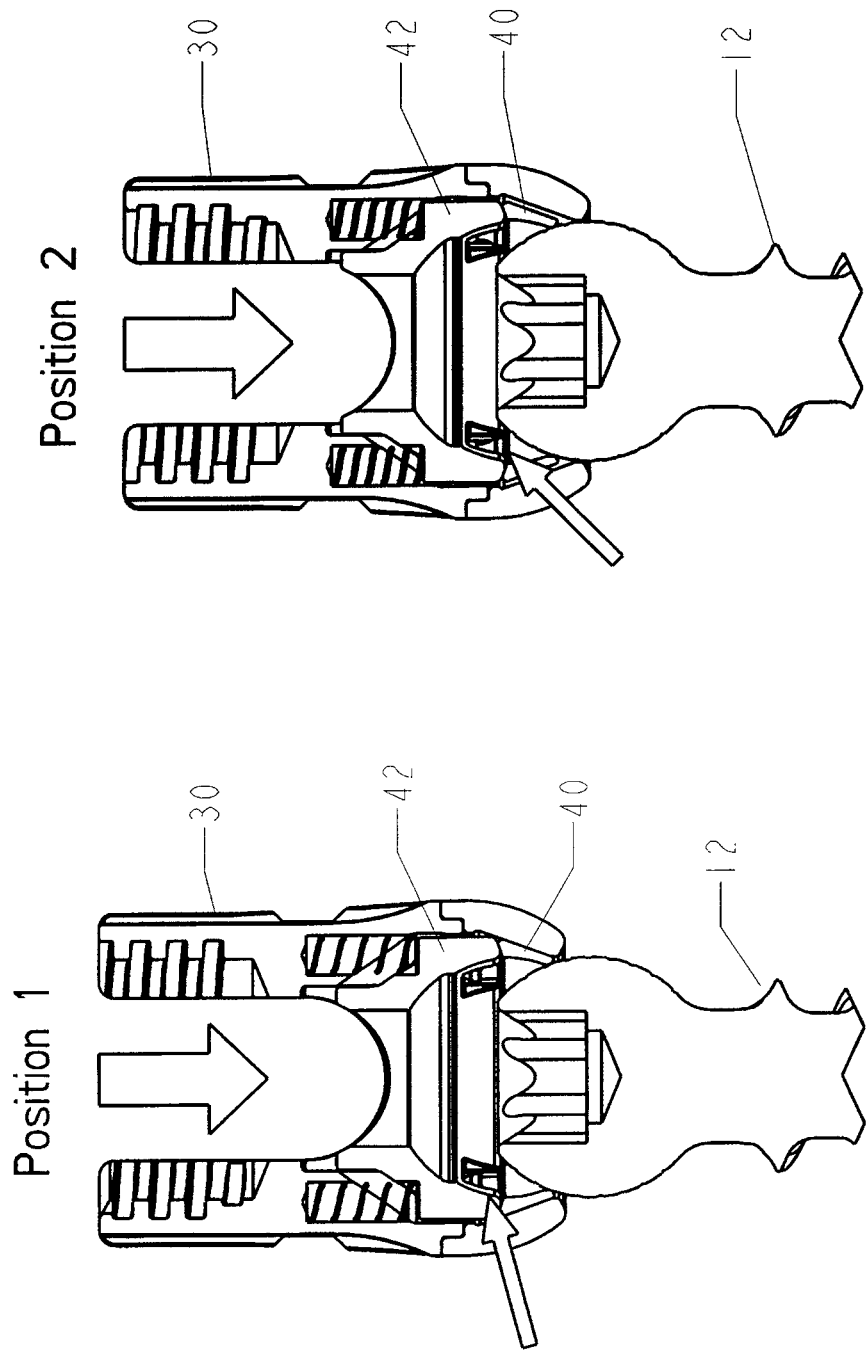

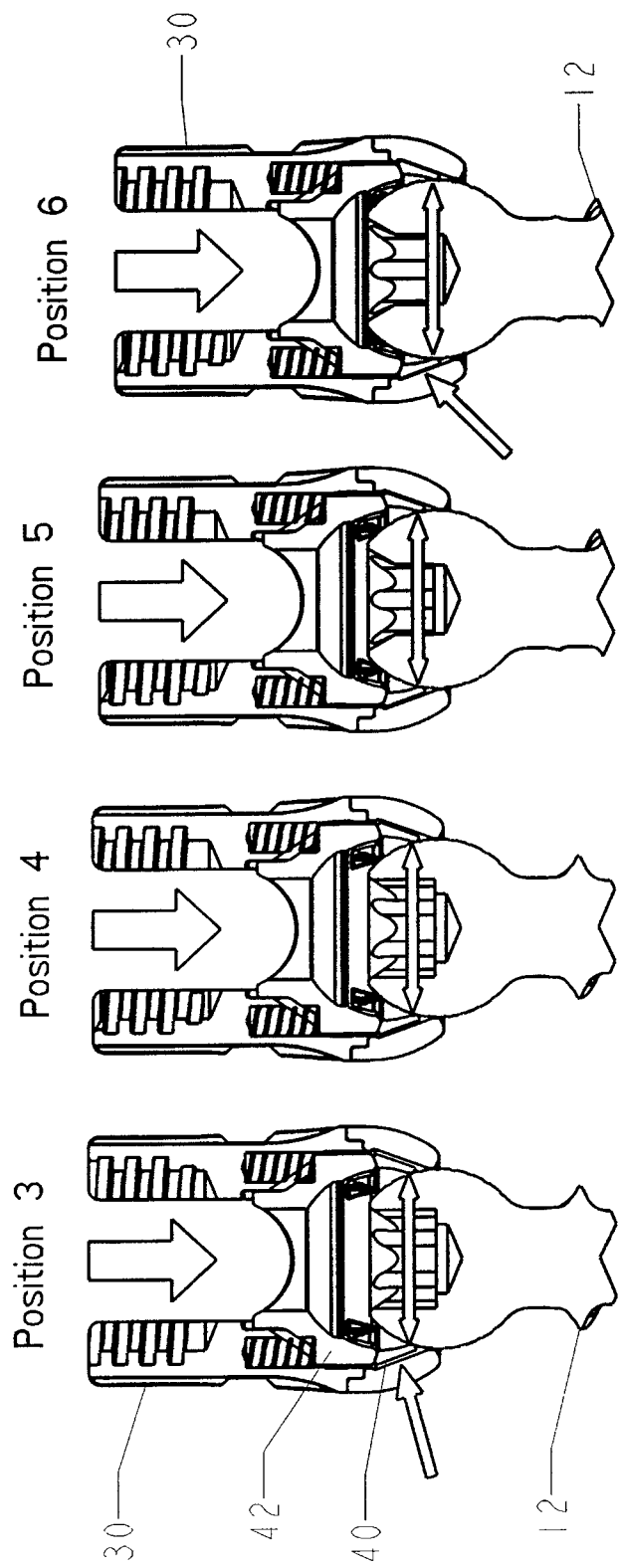

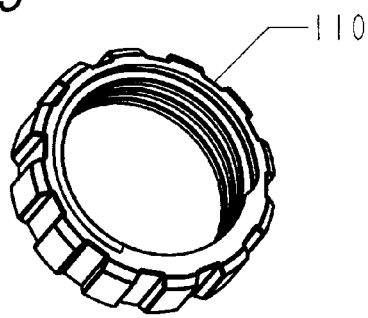
Fig. 25
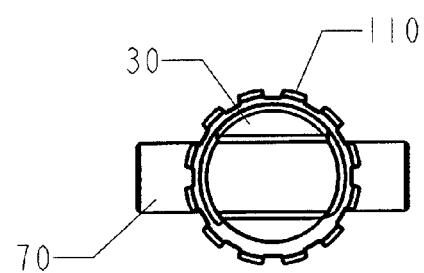
Fig. 24
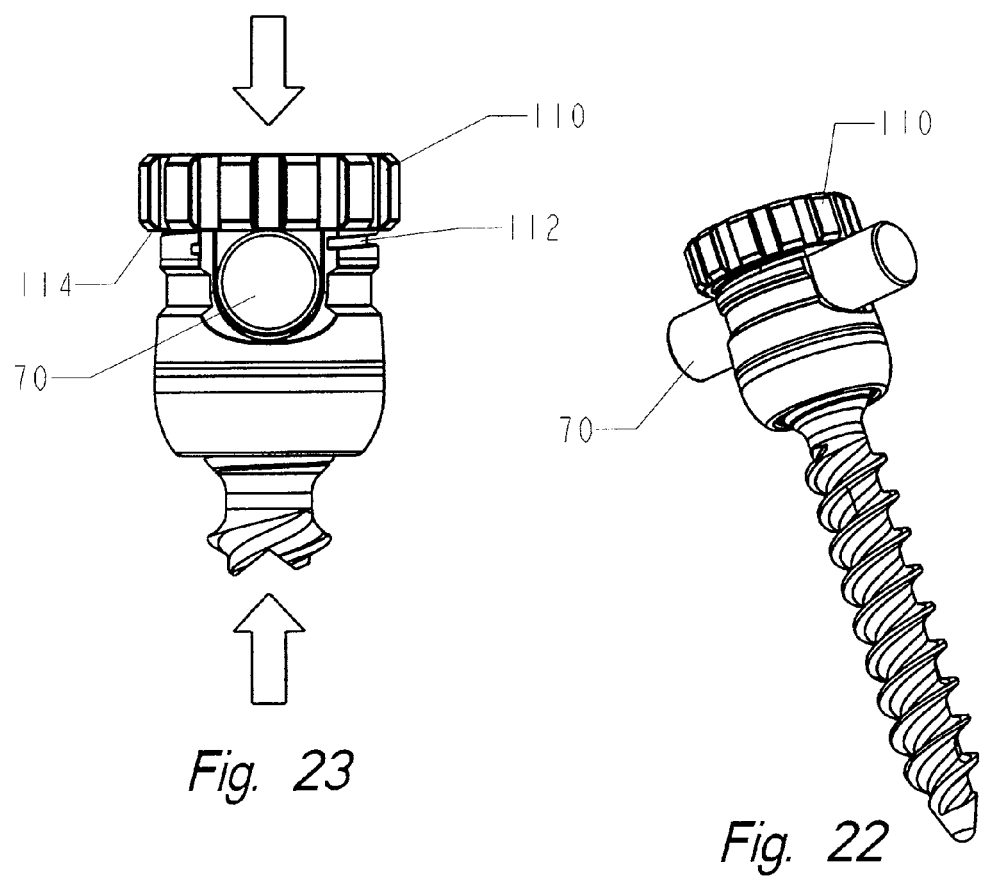
Fig. 23
Fig. 22

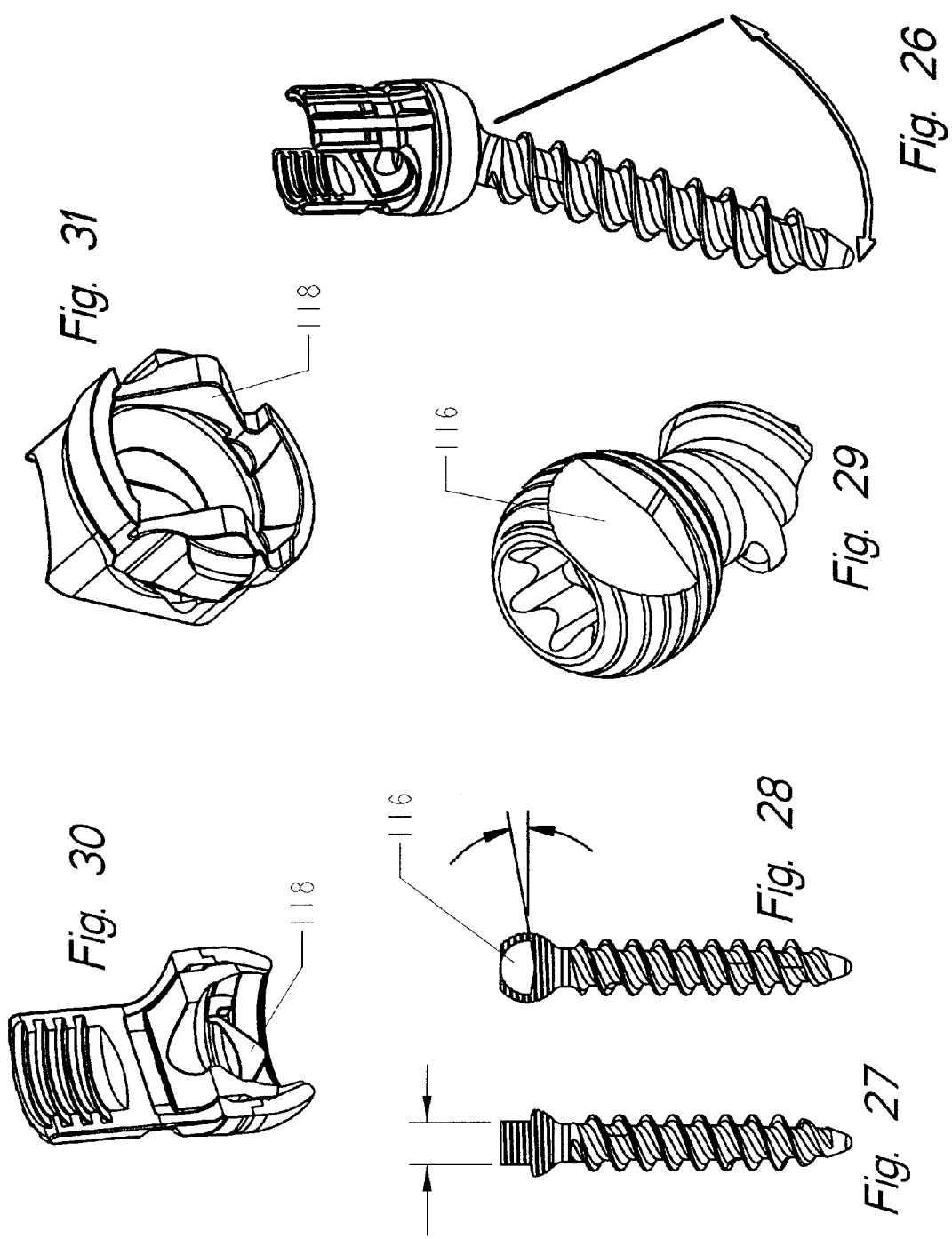

LOCKING POLYAXIAL BALL AND SOCKET FASTENER

CROSS REFERENCE TO RELATED APPLICATIONS

This application is a continuation of U.S. patent application Ser. No. 12/355,145 filed on Jan. 16, 2009 now U.S. Pat. No. 7,947,065, which claims the benefit of the filing date of U.S. Provisional Patent Application No. 61/114,515 filed on Nov. 14, 2008, the contents of which are herein incorporated by reference.

FIELD OF THE INVENTION

This invention is directed to the field of ball and socket fasteners, and in particular to a polyaxial ball and socket fastener adapted for use as a spinal implant.

BACKGROUND OF THE INVENTION

There are numerous ball and socket fasteners, however, when the application is applied to a particular product, the ball and socket must meet minimum specifications in order to be effective. For instance, in the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws are inserted into the patient's spinal bones, and a series of connectors are used to rigidly link the rods and anchors.

A variety of designs exist, with each design addressing various aspects of the difficulties that arise when one re-shapes an individual's spine to follow a preferred curvature. Known spinal implant systems often correct one set of problems only to create new ones.

Common to all spinal implant systems is the necessity for proper anchoring to the bone so as to provide support for the aforementioned components. While bone screws are commonly used for anchoring, the use of a polyaxial design has proven very effective in allowing a surgeon the flexibility to secure an installation with minimal strain on the individual.

For this and other reasons, screws located in bone structure typically use a polyaxial base and a specially designed connector member for attachment to a component such as an alignment rod. A problem with the current technology is that bone structure cannot be determined until the patient's bone is exposed. This problem requires a large inventory of various sized implants to be on hand during every surgery. The surgeon must search through the inventory to assembly a combination based on his prediction of what will be required. Even if an implant combination is predicted, the anchoring screw may still require angular insertion due to muscle structure or nerve locations. Any movement of muscle and other tissue increases the difficulty of the operation and can be a major trauma to the patient. Still yet, bone condition may require oversize threads to achieve a suitable purchase to the bone. As a consequence, the surgeon must either maintain a large inventory of anchoring devices, or have a vendor standing by with a large inventory of anchoring devices that will hopefully meet the individual requirements.

A conventional polyaxial bone screw typically consists of a single shaft with a coarse thread at one end for threading into the bone. A spherical ball is positioned at an opposite end for coupling to a connecting member. For example, a number of patents exist for bone screw anchoring assemblies that include a U-shaped connector element which acts as a saddle for attachment to an alignment rod. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion designed for threadingly engaging a semi-spherical cup for use with a specially designed alignment rod. The alignment rod includes spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are designed with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths.

U.S. Pat. No. 7,445,627 discloses a fastener and a bone fixation assembly for internal fixation of vertebral bodies. According to one exemplary embodiment, a tulip assembly is employed, the tulip assembly includes a non-circular surface disposed on its outer surface. A fastener is coupled to the tulip assembly and positionable to retain the tulip assembly on the head of a screw. A cap having an outer surface and a plurality of inner protrusions mateably connects to the non-circular surface on the tulip body to compress the tulip assembly to secure a rod.

U.S. Publication No. 2008/0177322 discloses a spinal stabilization system that includes bone fastener assemblies that are coupled to vertebrae. Each bone fastener assembly includes a bone fastener and a collar. The bone fastener has a head portion having at least a first cross-sectional shape in a first plane, and a second cross-sectional shape in a second plane. The collar has a circular opening in the bottom, with a relief extending from the circular opening. The second cross-sectional shape of the bone fastener is keyed to the opening to permit insertion of the bone fastener into the collar assembly from the bottom. After insertion, the bone fastener is rotated to prohibit removal of the bone fastener from the collar. The collar can then be rotated and/or angulated relative to the bone fastener. An elongated member can be positioned in the collar and a closure member is then used to secure the elongated member to the collar.

U.S. Publication No. 2006/0241599 discloses a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

U.S. Publication No. 2006/0235392 discloses a system for connecting a fastener element (e.g., a pedicle screw) relative to a rod for the purposes of vertebral fixation. The system may permit multi-axial movement between the fastener element and the rod. Further, the system may permit the angular relationship between the fastener element and the rod to be held in a desired orientation.

U.S. Publication No. 2006/0155277 discloses an anchoring element for securing a rod on a vertebra, that comprises a retaining means for receiving the rod, a safety element placed on the retaining means, a securing element which can be placed on the body of the vertebra, and a clamping device which is arranged between the retaining means and the securing element. The clamping device includes a ring-shaped mount, a partially conical-segment shaped bearing and an intermediate element which is embedded in the mount and which engages the bearing, whereby the mounting is moveable in a removed state in relation to the bearing, whereas the mount is maintained in a clamped state on the bearing by means of the intermediate element. The mount is rigidly connected to the retaining means and the bearing is rigidly connected to the securing element.

U.S. Publication No. 2006/0149240 discloses a polyaxial bone screw assembly that includes a threaded shank body having an upper capture structure, a head and a multi-piece retainer, articulation structure. The geometry of the retainer structure pieces correspond and cooperate with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body.

U.S. Pat. No. 6,716,214 discloses a polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head, at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

U.S. Pat. No. 6,565,567 discloses a pedicle screw assembly for use with a rod for the immobilization of bone segments. The assembly is comprised of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semi-cylindrical rod engaging surfaces to prevent the rod from rotating or sliding within the housing once the set screw is tightened. A set screw is threaded into the housing posts to secure the rod within the housing. The washer has a roughened lower surface which, in conjunction with the reduced cross-sectional area at the bottom of the housing, securely clamps and locks the housing to the screw head when the set screw is tightened.

U.S. Pat. No. 5,501,684 discloses an osteosynthetic fixation device which consists of a fixation element which has a conical head section and an anchoring element abutting it which is for attachment into the bone. The fixation device also consists of a spherically formed, layered, slotted clamping piece which has a conical borehole for installation of the conical head section, and which is meant for locking within a connecting piece equipped with a spherically shaped layered borehole. Fixation piece has an axially arrayed tension element, permitting axial displacement and wedging of conical head section in the borehole that corresponds with it. The fixation device is appropriate for use as a plate/screw system, an internal or external fixator, and in particular for spinal column fixation.

U.S. Pat. No. 4,693,240 discloses a bone pin clamp for external fracture fixation. The apparatus comprises rotation, slide and housing elements nested one within the next, each such element having an aperture to receive a pin therethrough, and the rotation and slide elements respectively affording pin adjustment in azimuth and zenith, and in height, relative to the housing element. A locking mechanism including a common actuator member is operable simultaneously to lock the pin and rotation and slide elements in the housing element. In a preferred form, the housing element serves as a cylinder with the slide element as a keyed piston therein, and the rotation element is a disc located between a screw and annular thrust members engaged in the piston, the piston and disc being split respectively to lock by expansion and compaction under screw action towards the thrust members.

U.S. Pat. No. 4,483,334 discloses an external fixation device for holding bone segments in known relation to each other. The device includes a pair of bone clamp assemblies each secured to bone pins extending from the bone segments, a bridge extending between the pin clamp assemblies, and a specialized high friction universal assembly connecting the bridge to each of the pin clamp assemblies.

U.S. Pat. No. 4,273,116 discloses an external fixation device for reducing fractures and realigning bones that includes sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

U.S. Pat. No. 6,672,788 discloses a ball and socket joint incorporating a detent mechanism that provides positive biasing toward a desired position. The ball and socket joint can be used in flexible supports that hold and support items such as lamps, tools and faucets. The detent mechanism comprises two corresponding parts, one in the ball portion and the second in the socket portion of the joint. The first detent part is a protrusion of some type and the second detent part is a groove or indentation that is adapted to accept and engage the protrusion. If the ball contains the detent protrusion, then the socket contains the detent indentation. And conversely, if the socket contains the detent protrusion, then the ball contains the detent indentation. The detent tensioning force can be provided by a spring or a spring band, the characteristics of the material from which the joint is made, or by some other similar tensioning device.

U.S. Publication No. 2003/0118395 discloses a ball and socket joint, which has a housing, a ball pivot mounted pivotably in the housing, and a sealing bellows, which is fastened to the housing and is mounted on the ball pivot slidably via a sealing ring provided with two legs. A first leg of the two legs is in contact with the ball pivot under tension and the second leg meshes with the wall of the sealing bellows. The second leg is, furthermore, fastened in an anchoring ring arranged at least partially in the wall of the sealing bellows.

U.S. Pat. No. 4,708,510 discloses a ball joint coupling assembly that permits universal movement and positioning of an object with respect to a vertical support shaft. Quick release/lock action is provided by a ball joint assembly having a housing in which a ball and piston are movably coupled. The ball is captured between annular jaw portions of the housing and piston, with locking action being provided by gripping engagement of the piston jaw portion and the housing jaw portion. The ball member is gripped in line-contact, compressive engagement by the annular edges of the piston jaw and housing jaw on opposite sides of the ball. The piston is constrained for axial movement within the housing with locking engagement and release being effected by rotation of a threaded actuator shaft.

U.S. Pat. No. 3,433,510 discloses a swivel structure for rigidly joining first and second parts together. A first member is connected to the first part and a second member is connected to the second part. An intermediate hollow member interconnects the first and second members together. An enlarged outer end portion is provided on the first member and includes a plurality of locking means thereon. Means are provided on the second member for engaging one of the locking means. Means are provided for threadably joining the hollow member and the second member together. A slot is provided in the hollow member and includes an enlarged entrance which passes the enlarged outer end portion and which also includes a restricted opening opposite the threaded joining of the hollow member and the second member together. The portion surrounding the restricted opening opposes the forces imparted against the outer end portion as the second member is threadably joined to the hollow portion and bears against the outer end portion.

U.S. Patent Publication No. 2008/0269809 discloses a bottom loading pedicle screw assembly. The device includes a pedicle screw and a connector member. The pedicle screw includes a threaded lower portion while the upper portion includes a groove sized to accept a clip member. The clip member includes a spherical outer surface. In operation the clip is placed within the groove and the assembly is pressed through the opening in the bottom of the connector member. While the device is bottom loading, the device will separate when the pedicle screw is aligned with the connector member. The construction of the clip member allows the clip to collapse sufficiently to pass back through the opening when the screw is positioned in alignment with the connector, requiring the connection to bone be placed at an angle with respect to the connector for proper operation.

Thus, what is needed is a lockable polyaxial ball and socket joint that can be adapted for use in a spinal fixation system that includes the advantages of known devices, while addressing the shortcomings that they exhibit. The system should allow component interchageability at point of installation, thereby addressing a wide variety of spinal deformities with less components.

SUMMARY OF THE INVENTION

Briefly, the present invention is a polyaxial ball and socket joint capable of snap together assembly and thereafter lockable into a fixed position. Disclosed is an exemplary embodiment of the ball and socket fastening system adapted for use in a spinal fixation system for reshaping the spine of a patient. The fixation system includes the polyaxial ball having a bone screw extending outwardly therefrom for use in anchoring to the spine and a connector member that includes a socket constructed and arranged to accept the polyaxial ball. In the disclosed embodiment, the connector member is illustrated as a U-shaped connector member having a lower receptacle that operates as a socket for housing an upper retainer ring and a lower split retaining ring. The socket is receptive to the spherical connector which is inserted through an aperture in the bottom of the connector assembly where the spherical polyaxial ball contacts the lower split retainer ring causing a momentary displacement thereof, allowing the ring to contact a plurality of ramps that are constructed and arranged to open the split ring allowing the ball to pass through the ring positioning of the spherical connector between the upper and lower retainer rings. A set screw or nut can then be utilized to press the upper retaining ring into contact with the ball while simultaneously causing the lower split ring to engage a lower portion of the ball as it wedges between the ball and the inner surface of the connector member immobilizing the connection.

This construction facilitates the receipt of the spherical connector into the bottom of the connector member, eliminating the requirement of inserting the screw and spherical connector through the top opening of the connector member. This construction also allows for the use of bone anchors that will not fit through the top opening of the connector member. In addition, the use of the dual retainer rings allows for the coupling of an anchor screw to a connector member during surgery, without the aid of tools. In this manner, during surgery a surgeon can determine the most advantageous bone screw, hook or other type of bone connection to match the most advantageous connecting assembly. The bone connector is then coupled to the connector assembly by inserting or snapping the spherical connector into the socket of the connecting assembly. In operation, the spherical connector is pushed past the lower retainer ring whereby the ring snaps past the largest diameter of the connector to prohibit removal of the connector while still allowing polyaxial movement between the spherical ball and the connector member. Because of the flexibility and resilience of the split retention ring, the mating parts do not require fine tolerances and are economical to manufacture. The system is modular, employing a collection of anchoring assemblies that are linked, via various connectors, to strategically-arranged stabilizing rods.

The connector members are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a lockable polyaxial ball and socket fastener.

It is another objective of the present invention to disclose the use of a lockable polyaxial ball and socket fastener for use in a spinal stabilization system.

Another objective of the invention is to disclose the use of a lockable polyaxial ball and socket system that is capable of securing various anchors to various connector members so as to reduce the amount of inventory required to meet a particular installation.

It is another objective of the present invention to provide a polyaxial bone screw assembly for a spinal fixation system that permits component adjustment during installation, thereby enabling satisfactory correction of a wide variety of spinal deformities.

It is an additional objective of the present invention to provide a bone screw assembly that includes a split ring locking mechanism that is simple, strong and reliable.

It is yet another objective of the present invention to provide a polyaxial bone screw that can be coupled to a reciprocal connecting member without tools.

It is yet another objective of the present invention to provide a spinal fixation system that require minimum tools for installing of an anchor and securing element.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 11 is a partial bottom perspective view of the connector member;

FIG. 12 is a partial top perspective view of the connector member;

FIG. 13 is a bottom view of the connector member;

FIG. 21A is a section view illustrating assembly of the spherical ball and the connector assembly;

FIG. 21B is a section view illustrating assembly of the spherical ball and the connector assembly;

FIG. 21C is a section view illustrating assembly of the spherical ball and the connector assembly;

FIG. 21D is a section view illustrating assembly of the spherical ball and the connector assembly;

FIG. 21E is a section view illustrating assembly of the spherical ball and the connector assembly;

FIG. 21F is a section view illustrating assembly of the spherical ball and the connector assembly;

FIG. 22 is a perspective view of an alternative embodiment of the instant invention;

FIG. 23 is a partial side view of the embodiment illustrated in FIG. 22;

FIG. 24 is a top view of the embodiment illustrated in FIG. 22;

FIG. 25 is a perspective view of a retaining nut;

FIG. 26 is a perspective view of an alternative embodiment of the instant invention having only mono-axial movement;

FIG. 27 is a front view of the bone anchor of the embodiment illustrated in FIG. 26;

FIG. 28 is a side view of the bone anchor of the embodiment illustrated in FIG. 26;

FIG. 29 is a partial perspective view of the spherical connector utilized in the mono-axial embodiment;

FIG. 30 is a partial section view of the connector assembly utilized in the mono-axial embodiment;

FIG. 31 is a lower perspective view of the upper retaining ring utilized in the mono-axial embodiment.

DETAILED DESCRIPTION OF THE PREFERRED EMBODIMENT

Figure 1:
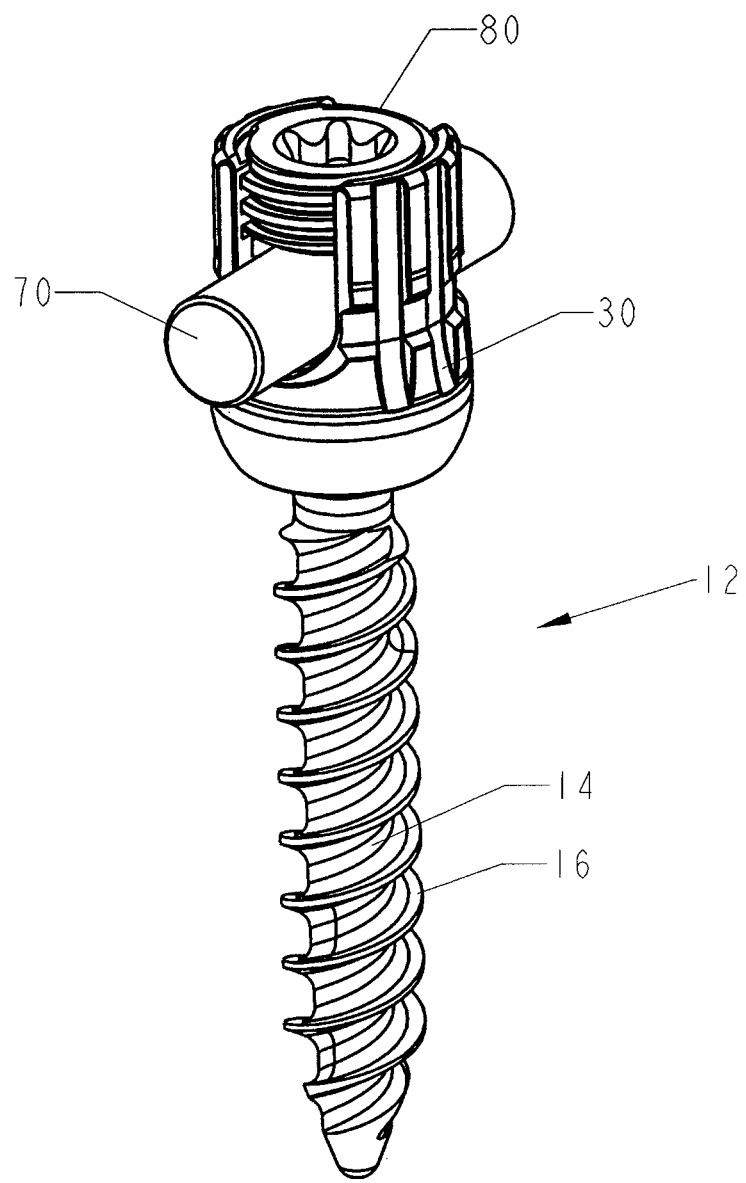
FIG. 1 is a top perspective view of the ball and socket fastener applied to a spinal fixation device.
Figure 2:
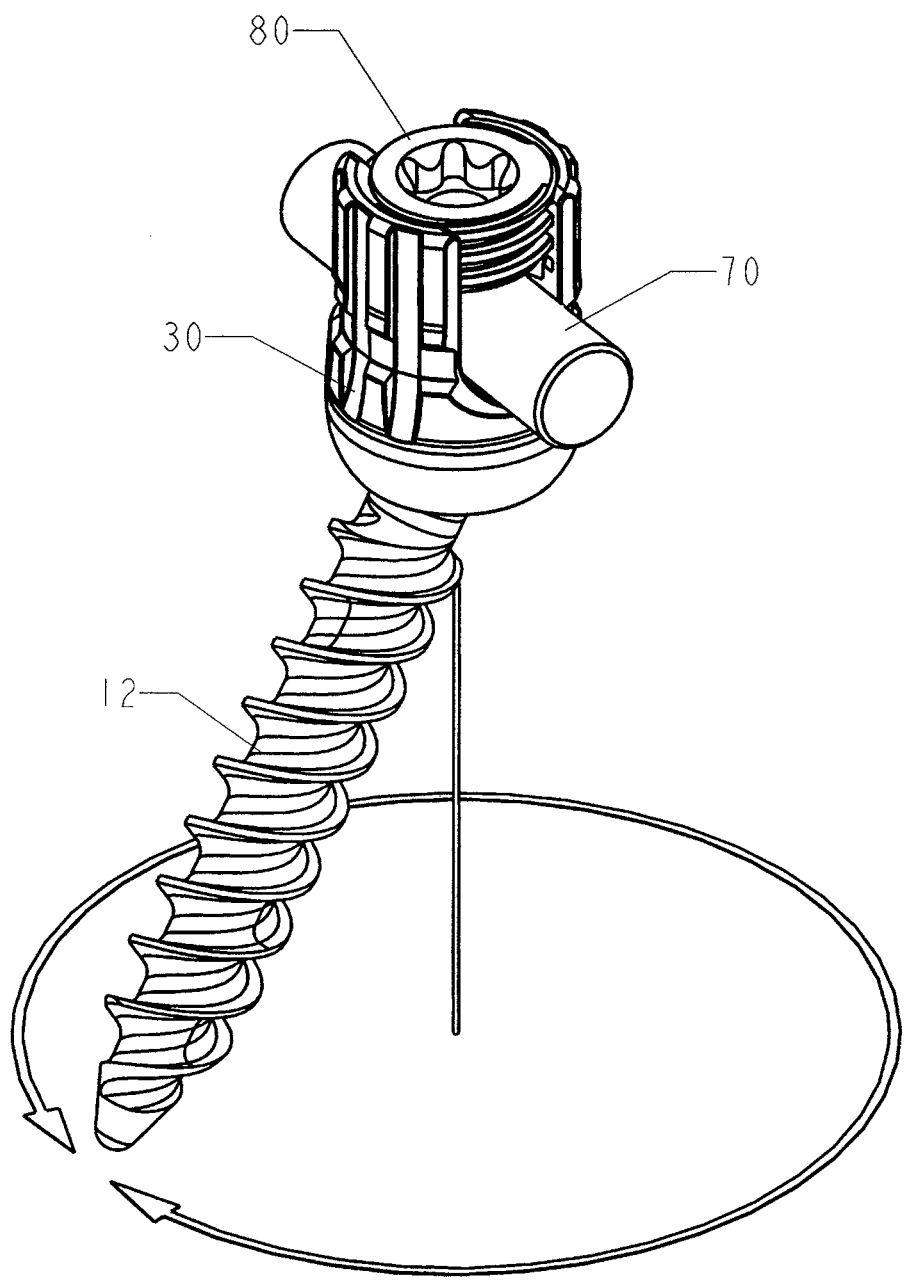
FIG. 2 is a top perspective view of the ball and socket fastener with the anchoring member illustrating the polyaxial cooperation between the spherical ball and the connector member.
Figure 3:
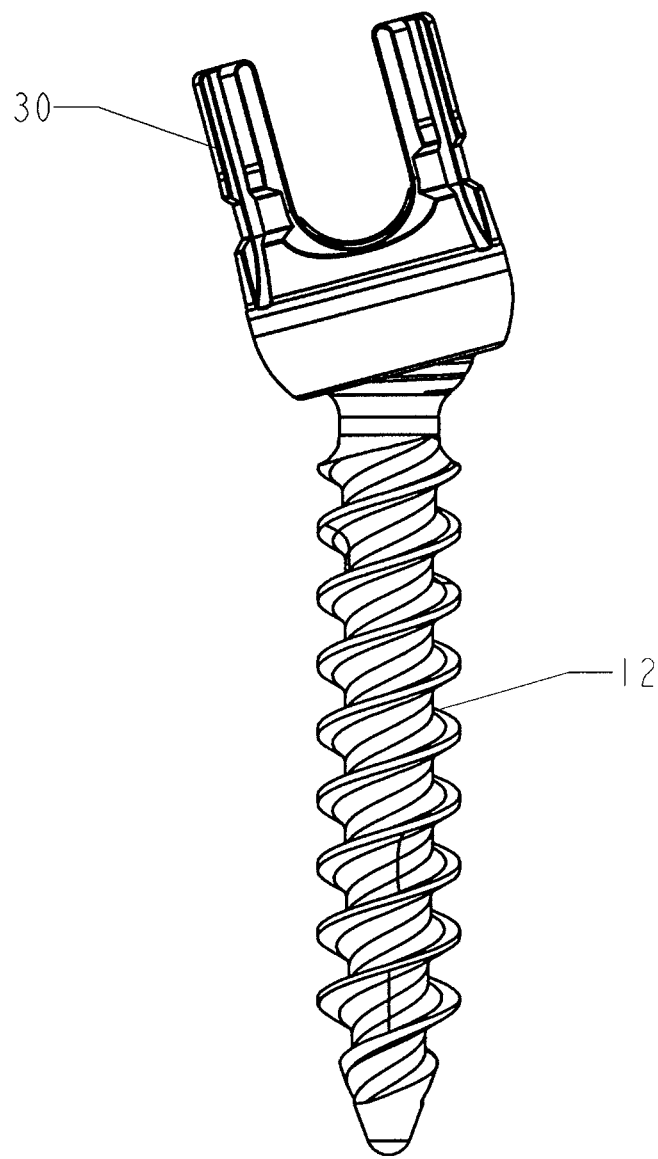
FIG. 3 is a side view of the ball and socket fastener.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the locking polyaxial ball and socket fastening system adapted for use in a spinal fixation system. The fastening system includes a spherical ball secured or formed integrally with a bone anchor and connecting assembly that includes a snap-in type receptacle (38) for the spherical ball to form a polyaxial joint. The connector assembly also includes a receiver that may be used in conjunction with a connecting rod member for securing at least two bone anchors together.

Figure 19:
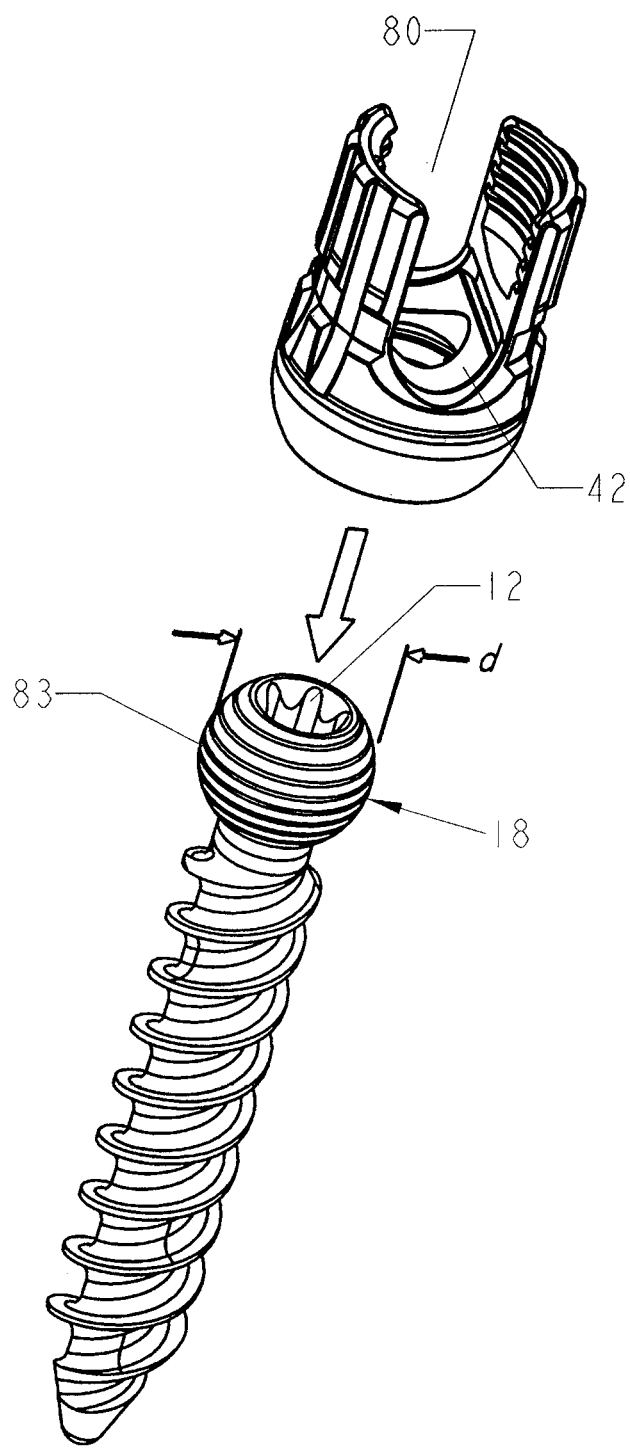
FIG. 19 is a perspective view illustrating assembly of the retaining assembly to the spherical connector.
Figures 20A, 20B, 20C, 20D, 20E, 20F, 20G, 20H:
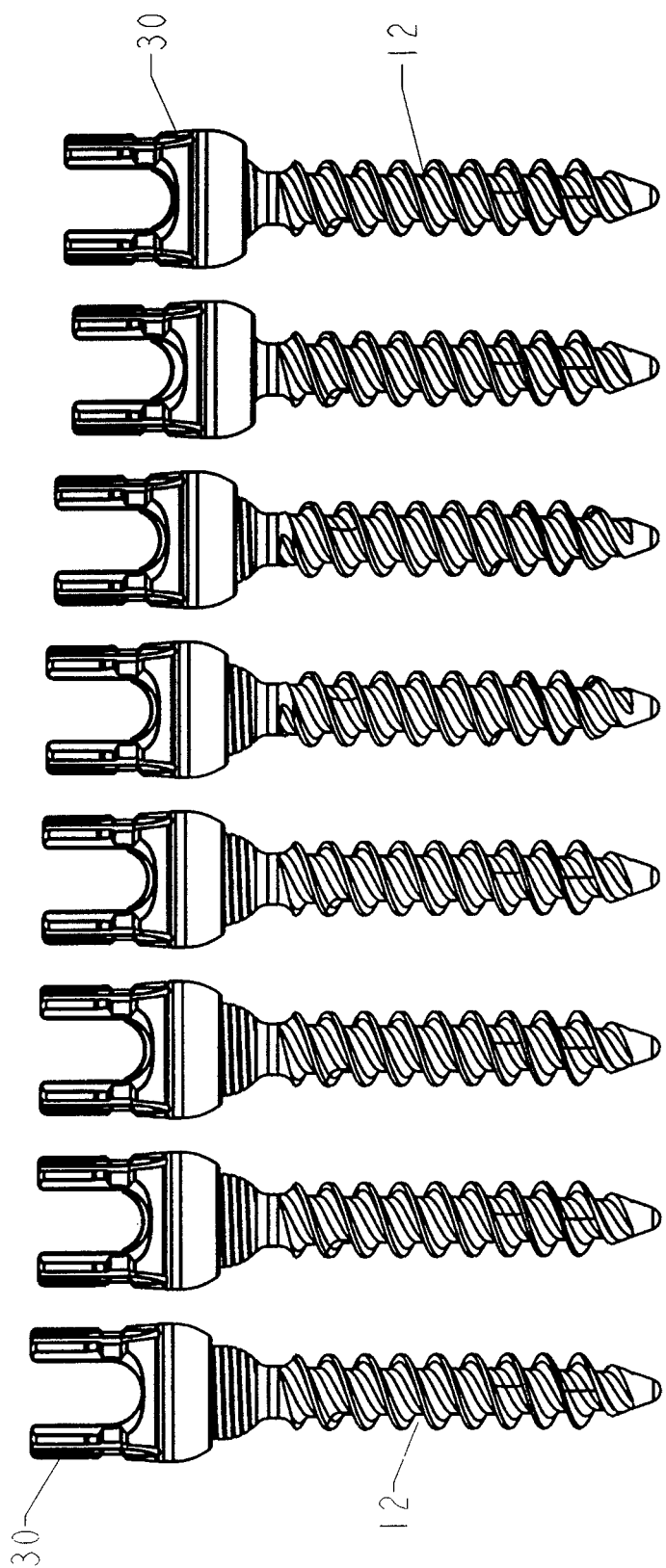
FIG. 20A is a side view illustrating assembly of the spherical ball and the connector assembly.
FIG. 20B is a side view illustrating assembly of the spherical ball and the connector assembly.
FIG. 20C is a side view illustrating assembly of the spherical ball and the connector assembly.
FIG. 20D is a side view illustrating assembly of the spherical ball and the connector assembly.
FIG. 20E is a side view illustrating assembly of the spherical ball and the connector assembly.
FIG. 20F is a side view illustrating assembly of the spherical ball and the connector assembly.
FIG. 20G is a side view illustrating assembly of the spherical ball and the connector assembly.
FIG. 20H is a side view illustrating assembly of the spherical ball and the connector assembly.

Referring to FIGS. 1-4 and 19, the bone anchor of the preferred embodiment is a bone screw (12) including a shank (14) having a length with at least one helical thread (16) formed along the length thereof. It is important to note that the proportions of the bone screw depicted are for illustrative purposes only and variations in the length of the shank, diameter of the screw, thread pitch, thread length, number of thread leads, shank induced compression and the like may be varied without departing from the scope of the invention. At the upper end (20) of the shank (14) is a ball shaped spherical connector (18) having a predetermined diameter (d) (FIG. 19). A driver receptacle (22) is located along the upper end (20) of the spherical connector for use in installing the bone screw by use of driving tool. It should be noted that the driving receptacle may be any shape, male or female, suitable for cooperation with a driving tool to rotate the bone screw into its final position.

Figure 14:
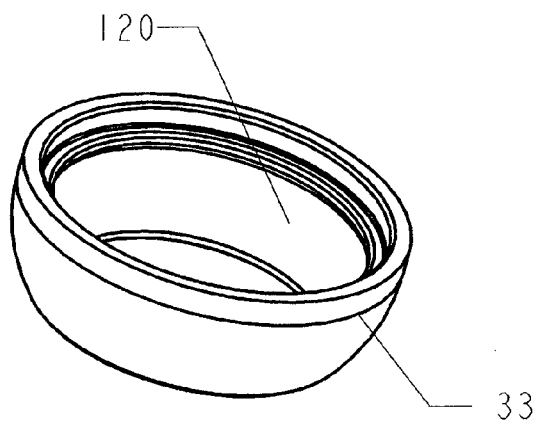
FIG. 14 is a top perspective view of the seat portion of the connector member.
Figure 15:
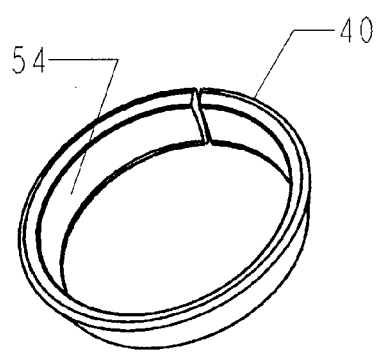
FIG. 15 is a perspective view of the lower split retaining ring.
Figure 16:
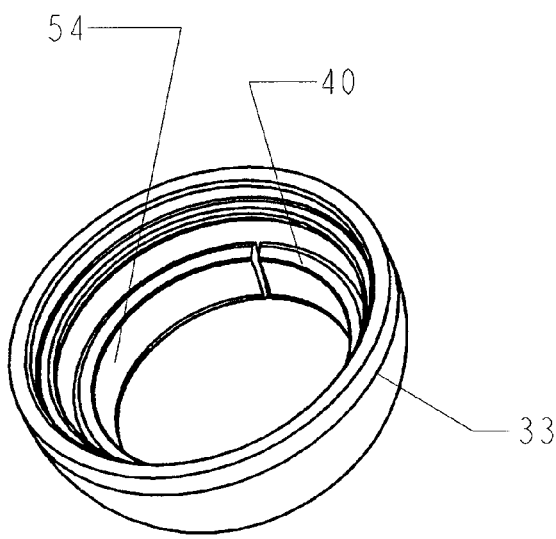
FIG. 16 is a perspective view illustrating the seat portion and the lower retaining ring.
Figure 17:
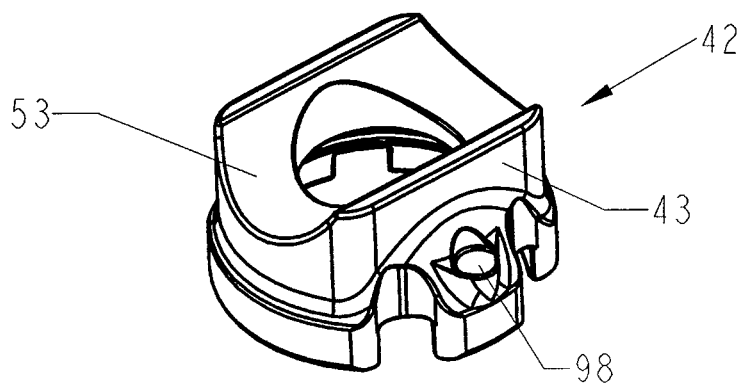
FIG. 17 is a top perspective view of the upper retaining ring.
Figure 18:
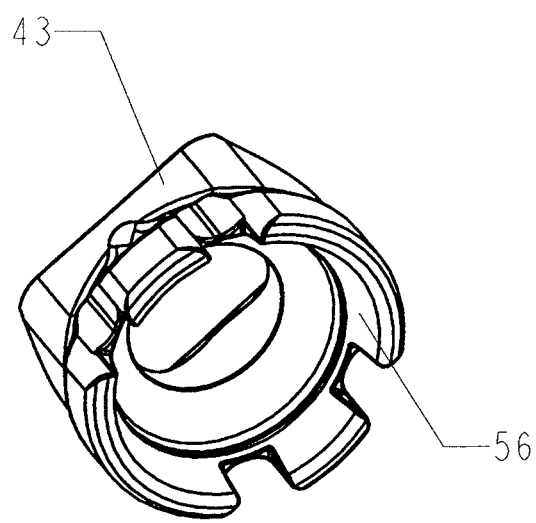
FIG. 18 is a lower perspective view of the upper retaining ring.

Referring to FIGS. 1-16, the U-shaped connector assembly is illustrated. The U-shaped connector assembly (30) includes an upper connector member (31) (FIGS. 11-13), a lower connector member (33) (FIG. 14), an upper retaining ring 42 and a lower split retaining ring (40) (FIG. 5). The upper connector member includes a substantially circular side wall (32) divided by a pair of U-shaped openings forming an upstanding first side wall (34) and second side wall (36). The side walls preferably include a plurality of recessed flutes (90). The flutes are constructed and arranged to provide a gripping surface that cooperates with a tool (not shown) to allow a physician to apply a counter torque to the connector member during tightening of the set screw (80) (FIG. 1). In addition to the flutes a groove (91) is cut around the perimeter of the connector member for attachment of an extender tube (not shown). Extender tubes are well known in the art of minimally invasive spinal procedures. The lower surface of the upper connector assembly includes a plurality of ramps (94) that are positioned to cooperate with the lower split retaining ring (40) during assembly to open the split ring so that the major diameter (d) (FIG. 19) of the spherical ball can pass through the ring (see FIGS. 21A-21H).

Referring to FIGS. 4-16, the upper connector member (31) preferably includes a shoulder (92) on the bottom surface thereof for location of the lower connector member (33). The lower connector member (33) also includes a shoulder 96 that is constructed and arranged to cooperate with shoulder (92) to maintain alignment of the two components. The lower connector member (33) includes a substantially spherical shaped lower receptacle (38) housing a lower split retainer ring (40) and upper retainer ring (42). The retainer rings (40, 42) are placed within the lower receptacle (38) during the manufacturing process. The shoulders (92) and (96) are utilized to align the components, and the upper and lower connector members are then laser welded together to prevent dislodgement of the retainer rings after assembly. It should be noted that other suitable methods or techniques of attaching the upper and lower connector members together may be utilized without departing from the scope of the invention, such methods may include, but should not be limited to spot welding, threads, adhesives, pins swaging, solder, interference fits and suitable combinations thereof.

Referring to FIGS. 5-13 and 17-18, the upper retainer ring (42) is illustrated. The upper retaining ring (42) is positioned within the lower receptacle (38) with an upper edge (52) positionable within the cavity formed by side wall (41); the upper retaining ring side wall (43) cooperates with side wall

(41) of the cavity to prevent rotation of the upper retaining ring. The inner surface (56) of the upper retaining ring provides for self centering by engaging of the outer surface of the spherical connector (18). The upper surface (53) of the upper retaining ring (104) preferably includes a concave cylindrical surface for cooperation with the connecting rod (70). The cylindrical surface provides additional surface area for contact with the connecting rod and may include a knurled or otherwise modified surface finish adapted to enhance gripping power between the rod and the connecting assembly (30). One embodiment of the upper retaining ring (42) includes spring pockets (98) that are located to cooperate with spring pockets (100) (FIG. 11) positioned in the upper connector member to locate and contain coil springs (102) (FIG. 5). The spring members bias the upper retaining ring toward the opening (50) of the lower receptacle.

Figure 21G:
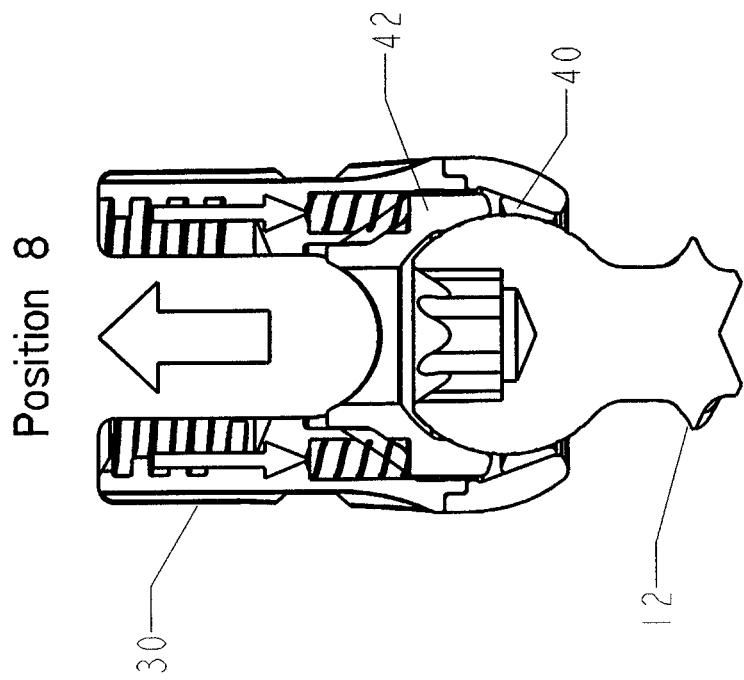
FIG. 21G is a section view illustrating assembly of the spherical ball and the connector assembly.
Figure 21H:
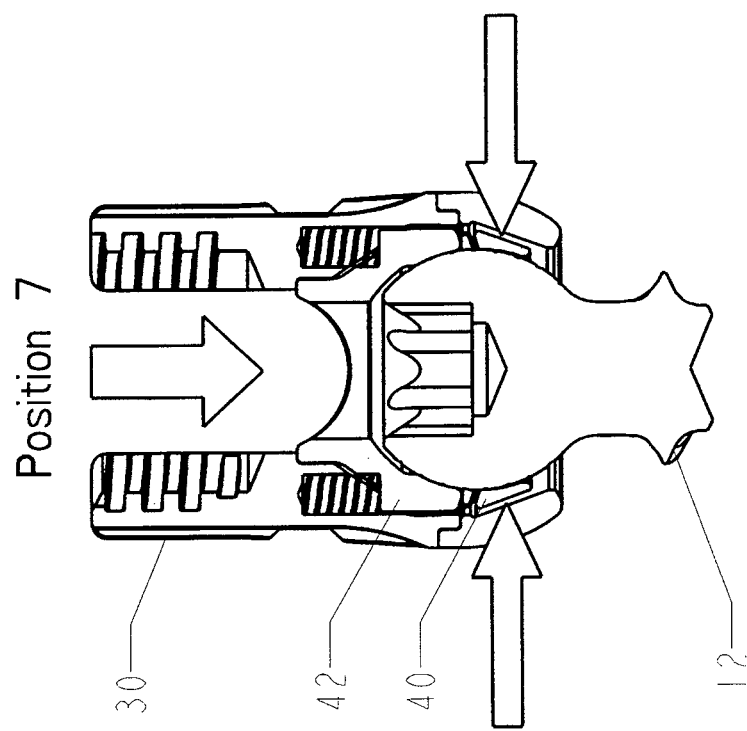
FIG. 21H is a section view illustrating assembly of the spherical ball and the connector assembly.

Referring to FIGS. 19-21H, assembly of the locking polyaxial ball and socket fastener is illustrated. Prior to assembly, the bone anchor 12 may be inserted into bone in a normal fashion without the connector member attached thereto. This allows the physician to a clear visualization of the screw as it is rotated into the bone. After insertion of the bone screw, the spherical connector (18) of the bone anchor (12) is inserted through the opening (50) (FIG. 21A) wherein the spherical connector (18) contacts the lower retainer ring (40). The lower retaining ring is pushed into contact with the upper retaining ring (FIG. 21B) thereby collapsing the springs 102 to cause the lower retaining ring to contact the ramps 94 (FIG. 21C). The cooperation of the ramps with the upper surface of the lower retaining ring causes the lower retaining ring to open up in diameter to snap over the major diameter (d) of the ball (FIGS. 21D-21F). Once the lower ring is opened sufficiently, the springs (102) move the ring to the lower portion of the lower receptacle thereby preventing the ball from being removed from the lower receptacle while still allowing polyaxial movement of the connector assembly with respect to the screw (FIGS. 21G-21H). Locking the ball and socket connection into a desired position is thereafter accomplished by placing a connecting rod (70) into the connector assembly so that it contacts the upper surface (53) of the upper retaining ring. A securing element in the form of a set screw (80) is inserted into the threaded portion of the upper retaining member until the set screw contacts the rod (70), causing the rod to move the upper retaining ring into contact with the spherical ball (18). The movement causes the ball to move toward the opening (50), wedging the lower split retaining ring 40 between the inner surface (120) (FIG. 14) of the lower retaining ring and the ball, locking the assembly in a desired position. It should be appreciated that this construction provides two rings of contact between the connector assembly and the spherical ball. The first ring of contact is provided by the upper retaining ring (42) and the second ring of contact is provided by the lower retaining ring (40). It should be noted that while the springs (102) are illustrated as coil springs, any spring or resilient type member suitable for displacing the split retaining ring may be utilized without departing from the scope of the invention. Such spring or resilient members may include, but should not be limited to, Belleville type springs, leaf springs, polymeric members and suitable combinations thereof.

Unique to this invention is the ability for the surgeon to attach various types of bone anchors or the like to the connecting assembly. While there is a myriad of anchoring devices that can be adapted to include the spherical ball, bone hooks etc., for ease of illustration the bone screw is depicted and it is well known that various lengths and diameters of bone screws are available, many of which would not fit through the inner diameter of the connector assembly. Thread styles, lengths and so forth the best suited for installation may be estimated before surgery but it is well known that only during actual surgery can the proper style be confirmed. Because it is most difficult to predict the proper combination of anchor screw and connector member, surgeons must either have a large selection of spinal implants to choose from or be forced to use the closest combination and hope that it will suffice.

It should be noted that while various types of bone screws have been mentioned, the instant installation allows placement of an anchoring device having a spherical connector into position before a connector member is attached. This provides the surgeon with an option of positioning the bone screw before placement of the connecting member thereby providing a simplified installation should positioning of the anchoring screw be difficult due to muscle or other interference. Installation of a bone screw with the connecting member allows a range of mobility as well as better visual positioning. Further, while the U-shaped connector member is depicted, various types of connector members may be used in combination with the spherical connector (18) allowing a surgeon to select the appropriate combination during surgery thereby enhancing the success for the benefit of the patient as well as lowering cost of inventory necessary when estimating the various types of situations that the surgeon may encounter during the operation.

It should also be noted that while only the lower retaining ring is illustrated as being split, the upper ring may also be split to facilitate placement into the lower receptacle without the need to weld the upper and lower portions of the retainer assembly together.

Referring to FIG. 19, the outer surface (83) of the spherical connector (18) may include a ridged style surface for enhanced frictional engagement. It should also be noted that the spherical connector is preferably sized only for insertion through the bottom opening (50) of the connector assembly and would not fit through the connector member opening (80) even if the upper retainer ring (42) was removed. This entry is a departure from conventional prior art which typically places the shank of a bone screw through the connector member wherein the opening along the bottom of the connector is sized to prevent passage of the spherical connector.

Figure 4:
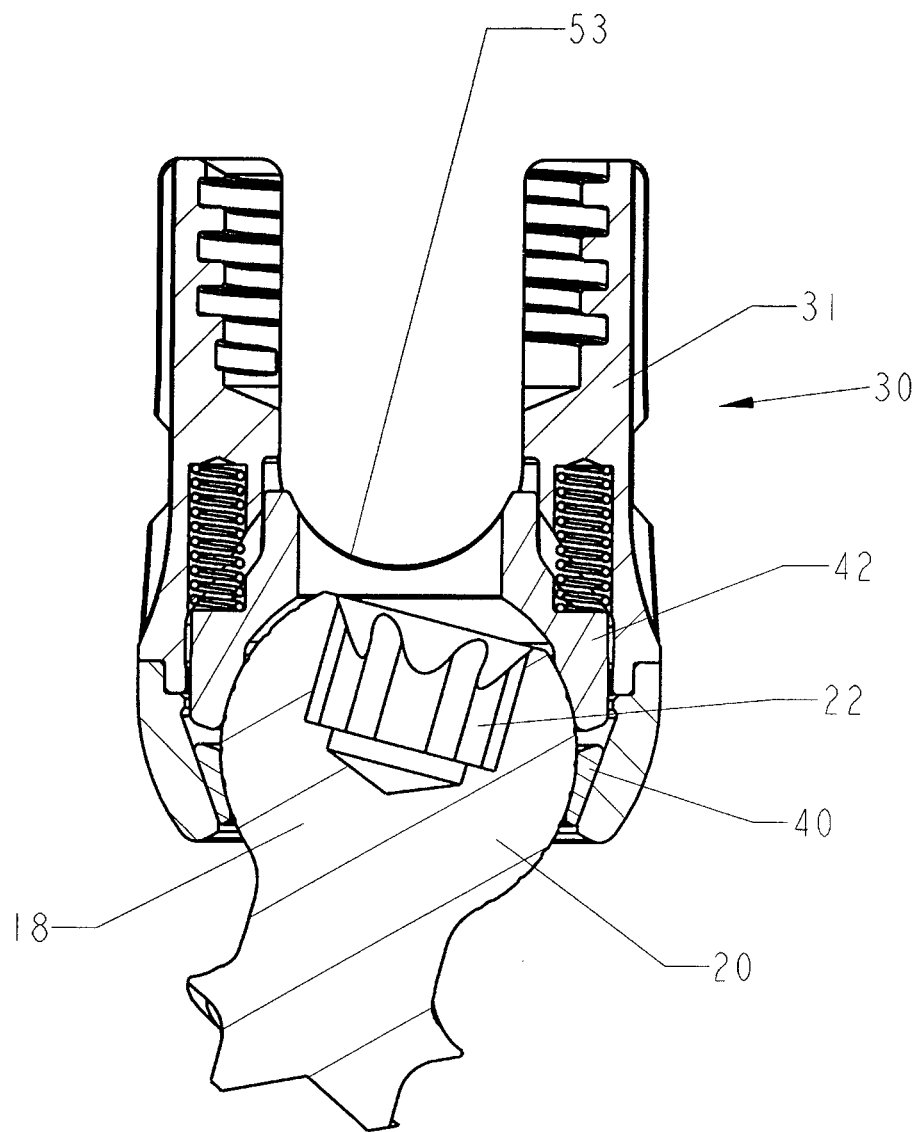
FIG. 4 is a partial section view of the ball and socket fastener.
Figure 5:
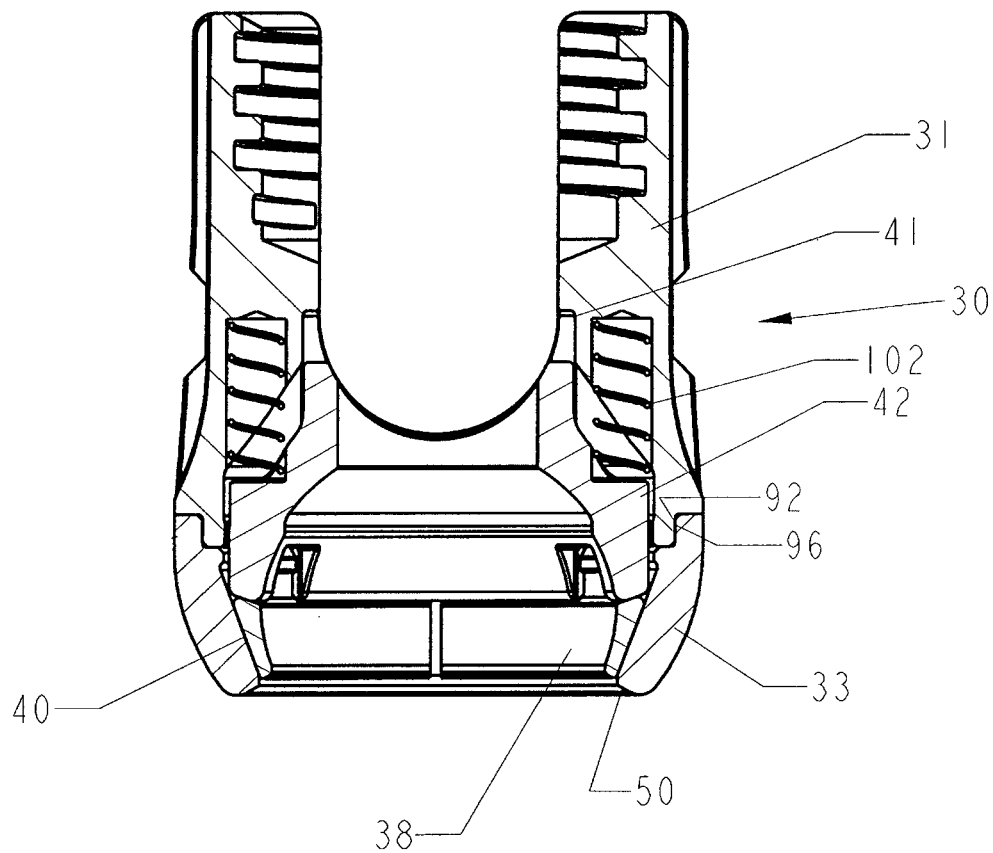
FIG. 5 is a section view of the connector assembly.
Figure 6:
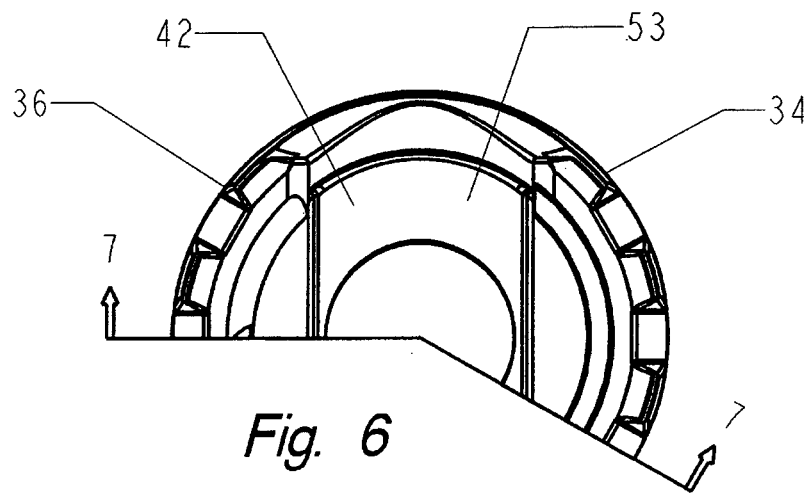
FIG. 6 is a top section view of the connector assembly.
Figure 7:
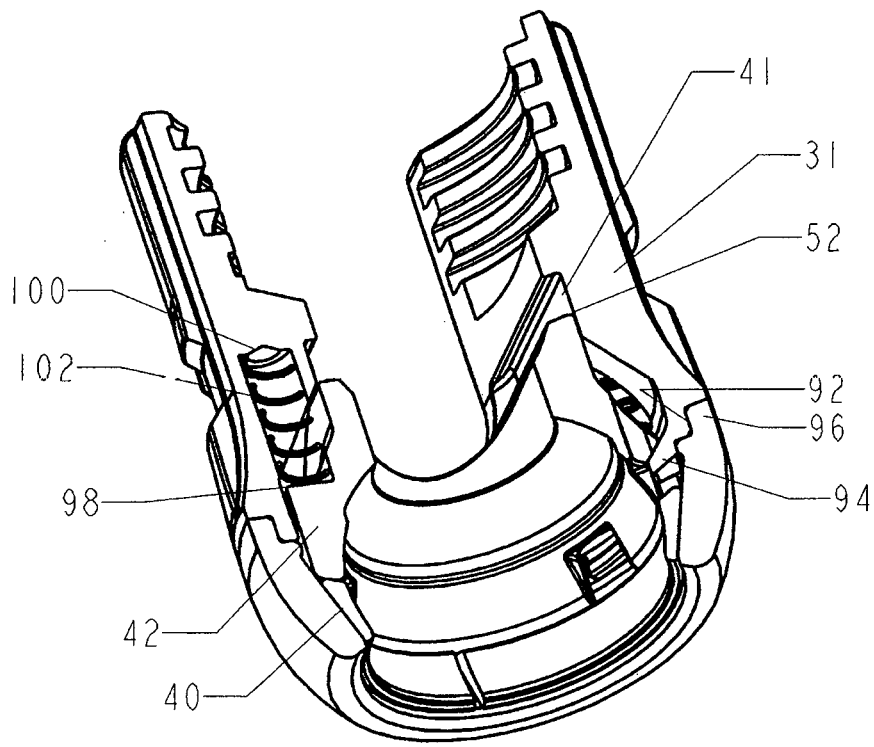
FIG. 7 is a perspective section view of the connector assembly taken along lines 7-7 of FIG. 6.
Figure 8:
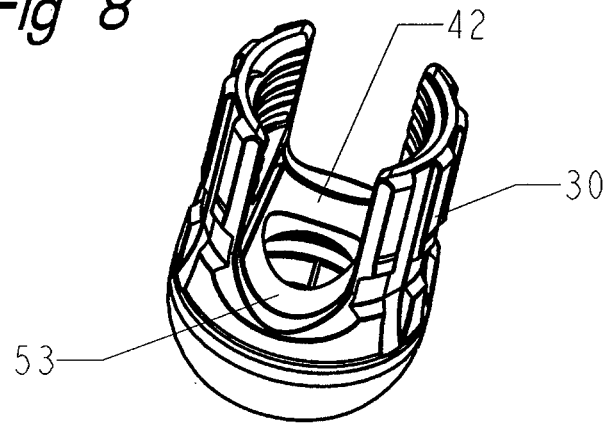
FIG. 8 is a top perspective view of the connector assembly.
Figure 9:
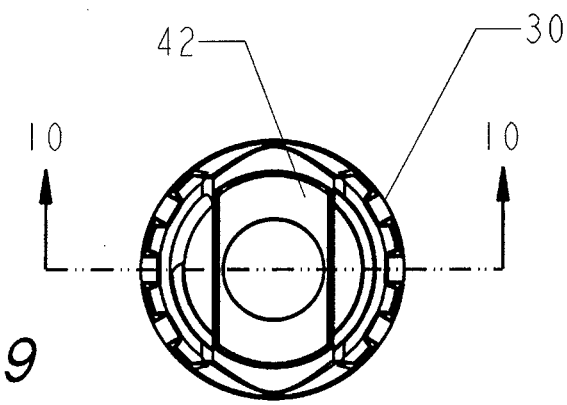
FIG. 9 is a top view of the connector assembly.
Figure 10:
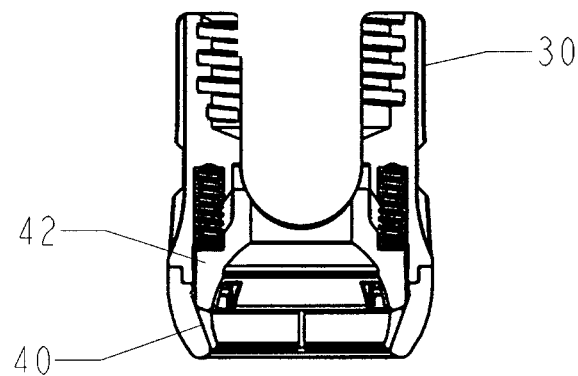
FIG. 10 is a section view of the connector assembly taken along lines 10-10 of FIG. 9.

Referring to FIGS. 4 and 19, the fastener receptacle (22) can be made of various shapes with the emphasis of providing a shank or a conventional fastener tool that provides the greatest amount of torque with minimal amount of slippage during installation. The inner surface (54) (FIGS. 15-16) of the lower retainer ring (40) is shown with a minimal portion of the surface engaging the spherical connector (18) during installation. However, once the spherical connector is positioned, the majority of the inner surface (54) of the lower split retaining ring (40) will engage the spherical connector (18) for optimal friction engagement. Similarly, the inner surface (56) of the upper retainer ring (42) (FIG. 18) engages the spherical connector (18) for frictional engagement. Preferably the inner surfaces (54 and 56) include a ridged surface that cooperates with the ridged surface (83) of the spherical connector (18).

Referring to FIGS. 22-25, an alternative embodiment of the instant invention is illustrated. In this embodiment, the set screw (80) is replaced by a threaded nut (110). The threaded nut includes internal helical threads constructed and arranged to cooperate with external threads (112) formed on the outer surface of the upper connector member (31). The threaded nut (110) includes a bottom surface (114) that engages the rod member (70), thereby causing the upper retainer member (42)

to engage the spherical connector (18) to wedge the lower retaining ring (40) between the spherical connector and the inner surface (120) of the lower connector member (33) to lock the position of the spherical connector with respect to the connector assembly.

Referring to FIGS. 26-30, an alternative embodiment of the instant invention is illustrated having mono-axial movement (see FIG. 26) in place of the polyaxial movement of the embodiments described above. Bone anchors that provide mono-axial movement, e.g. along a single axis, instead of polyaxial movement, e.g. motion along several different axes, are often desired for certain types of the spinal ailments such as, but not limited to, scoliosis. To limit the movement of the ball and socket fastener to a single axis, the spherical connector (18) includes, at least one, and more preferably a pair of guide(s) surface(s) (116) positioned on opposite side sides of the spherical connector (18) (FIG. 27). The guide surfaces (116) cooperate with rails 118 positioned within the inner surface (56) of the upper retaining ring (42). The rails (118) and the guide surfaces (116) cooperate to prevent substantial rotation of the spherical connector (18) while allowing movement of the bone anchor (12) along a single axis (FIG. 26).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A ball and socket fastener comprising:
an anchoring member having a shank and a spherical connector;
a connecting assembly having a socket constructed and arranged for receipt of said spherical connector along a first end defined by a first inner diameter and a securing element securable to a second end, an upper retainer ring having an outer diameter greater than said first inner diameter of said socket, said upper retainer ring disposed within said socket and positionable along an upper surface of said spherical connector, a floating lower retainer ring disposed within said socket and positionable along a lower surface of said spherical connector so that said connecting assembly moves polyaxially with respect to said anchoring member, said securing element traversable between an unlocked position and a locked position for controlling said polyaxial movement;
wherein said spherical connector head is received through said first end and positioned between said upper and said lower retainer rings.

2. The ball and socket fastener of claim 1 wherein said lower retainer ring includes a split to allow said lower retainer ring to expand in diameter.

3. The ball and socket fastener of claim 2 wherein said connecting assembly includes at least one ramp surface positioned to cooperate with said lower retainer ring during securement of said spherical connector to said socket to expand said lower retaining ring to pass a major diameter of said spherical connector.

4. The ball and socket fastener of claim 1 wherein said connecting assembly includes a substantially U-shaped opening sized to accept a rod member, an upper surface of said retaining ring including a rod engaging surface extending into said U-shaped opening, wherein said locked position of said securing element traverses said upper retainer ring to frictionally engage said spherical connector.

5. The ball and socket fastener of claim 4 wherein said upper retaining ring includes a cylindrically concave upper surface for cooperation with a connecting rod member.

6. The ball and socket fastener of claim 4 wherein said locked position causes said lower retaining ring to engage an inner surface of said connector and said lower portion of said spherical connector to immobilize said spherical connector.

7. The ball and socket fastener of claim 1 wherein said shank includes at least one helical thread.

8. The ball and socket fastener of claim 1 wherein said second end of said connecting assembly includes an internal thread and said compression element is further defined as a set screw.

9. The ball and socket fastener of claim 1 wherein said second end of said connecting assembly includes an external thread and said compression element is further defined as a nut having internal threads.

10. The ball and socket fastener of claim 1 including a biasing member positioned between said upper retaining ring and said lower retaining ring.

11. A ball and socket fastener comprising:
an anchoring member having a shank and a spherical connector, said spherical connector including at least one guide surface;
a connecting assembly having a socket constructed and arranged for receipt of said spherical connector along a first end defined by a first inner diameter and a securing element securable to a second end, an upper retainer ring having an outer diameter greater than said first inner diameter of said socket, said upper retainer ring disposed within said socket and positionable along an upper surface of said spherical connector, said upper retaining ring including at least one rail positioned to cooperate with said at least one guide surface, a floating lower retainer ring disposed within said socket and positionable along a lower surface of said spherical connector, said at least one guide surface and said at least one rail cooperating so that said connecting assembly moves mono-axially with respect to said anchoring member, said securing element traversable between an unlocked position and a locked position for controlling said mono-axial movement;
wherein when said spherical connector head is received through said first end and positioned between said upper and said lower retainer rings, said upper and lower retainer rings are spaced apart and said lower retainer ring is wedged without deformation between an inner surface of the connecting assembly and the spherical connector, locking the assembly in a desired position.

12. The ball and socket fastener of claim 11 wherein said lower retainer ring includes a split to allow said lower retainer ring to expand in diameter.

13. The ball and socket fastener of claim 11 wherein said connecting assembly includes at least one ramp surface positioned to cooperate with said lower retainer ring during securement of said spherical connector to said socket to expand said lower retaining ring to pass a major diameter of said spherical connector.

14. The ball and socket fastener of claim 11 wherein said connecting assembly includes a substantially U-shaped opening sized to accept a rod member, an upper surface of said retaining ring including a rod engaging surface extending into said U-shaped opening, wherein said locked position of said securing element traverses said upper retainer ring to frictionally engage said spherical connector.

15. The ball and socket fastener of claim 14 wherein said upper retaining ring includes a cylindrically concave upper surface for cooperation with a connecting rod member.

16. The ball and socket fastener of claim 14 wherein said locked position causes said lower retaining ring to engage an inner surface of said connector and said lower portion of said spherical connector to immobilize said spherical connector.

17. The ball and socket fastener of claim 11 wherein said shank includes at least one helical thread.

18. The ball and socket fastener of claim 11 wherein said second end of said connecting assembly includes an internal thread and said compression element is further defined as a set screw.

19. The ball and socket fastener of claim 11 wherein said second end of said connecting assembly includes an external thread and said compression element is further defined as a nut having internal threads.

20. The ball and socket fastener of claim 11 including a biasing member positioned between said upper retaining ring and said lower retaining ring.

21. A polyaxial ball and socket joint that can be locked into a fixed position comprising:
an anchoring element having a spherical connector, said spherical connector operating as a pivot point about which a connecting assembly is movable in a polyaxial fashion, said connecting assembly having a lower receptacle which operates as a socket for housing an upper retainer ring and a floating lower split retaining ring, said socket receptive to said spherical connector which is inserted through said lower split retainer ring causing a momentary displacement thereof which allows for the positioning of said spherical connector between said upper and said lower retainer rings.

22. The ball and socket fastener of claim 21 wherein said connecting assembly includes at least one ramp surface positioned to cooperate with said lower retainer ring during securement of said spherical connector to said socket to expand said lower retaining ring to pass a major diameter of said spherical connector.

23. The ball and socket fastener of claim 21 wherein said upper retaining ring includes a cylindrically concave upper surface for cooperation with a connecting rod member.

24. The ball and socket fastener of claim 21 wherein said lower retaining ring is constructed and arranged to engage an inner surface of said connector and said lower portion of said spherical connector to immobilize said spherical connector.

25. The ball and socket fastener of claim 21 including a biasing member positioned between said upper retaining ring and said lower retaining ring.

* * * * *